United States Patent
Langhauser

(10) Patent No.: US 7,452,425 B1
(45) Date of Patent: Nov. 18, 2008

(54) CORN REFINING PROCESS

(75) Inventor: Leon H. Langhauser, Decatur, IL (US)

(73) Assignee: Langhauser Associates, Inc., Decatur, IL (US)

( * ) Notice: Subject to any disclaimer, the term of this patent is extended or adjusted under 35 U.S.C. 154(b) by 516 days.

(21) Appl. No.: 11/336,324

(22) Filed: Jan. 20, 2006

Related U.S. Application Data

(63) Continuation-in-part of application No. 10/400,020, filed on Mar. 25, 2003, now abandoned.

(51) Int. Cl.
*C12P 7/06* (2006.01)

(52) U.S. Cl. ............... 127/40; 127/24; 127/27; 127/38; 127/68; 426/482; 435/94; 435/96; 435/161

(58) Field of Classification Search ............ 127/24, 127/27, 38, 40, 68; 426/482; 435/94, 96, 435/161
See application file for complete search history.

(56) References Cited

U.S. PATENT DOCUMENTS

| | | | |
|---|---|---|---|
| 4,361,651 A | 11/1982 | Keim | 435/161 |
| 6,254,914 B1 | 7/2001 | Singh et al. | 426/482 |

*Primary Examiner*—David A Reifsnyder
(74) *Attorney, Agent, or Firm*—Philip L. Bateman

(57) ABSTRACT

A grain containing starch, such as corn, is refined. The grain is steeped in water at a temperature of about 125 to 160° F., which water is essentially free of sulfurous acid and contains recycled enzymes from downstream processes, in a countercurrent steeping reactor for about 10 to 20 hours to produce an aqueous slurry of steeped grain having a moisture content of about 40 to 50 percent. The various components of the grain are then separated and the starch is converted to ethanol.

20 Claims, 8 Drawing Sheets

CORN REFINING PROCESS

CROSS-REFERENCE TO RELATED APPLICATION

This application is a continuation-in-part of U.S. patent application Ser. No. 10/400,200, filed Mar. 25, 2003, now abandoned.

FIELD OF THE INVENTION

This invention relates to chemistry. More particularly, this invention relates to food processing. Still more particularly, this invention relates to corn refining.

BACKGROUND OF THE INVENTION

1. Corn

Corn is the most important crop grown in the United States. Corn is sometimes called maize and has the scientific name *Zea mays*. Corn has a growing season of about four to six months. A mature corn plant consists of a stalk with an ear of corn. The ear of corn consists of about 800 kernels, or seeds, on a cylindrical cob. The kernels are eaten whole and are also processed into a wide variety of food and industrial products.

In more detail, the corn kernel consist of three main parts: (1) the pericarp; (2) the endosperm; and (3) the germ. The pericarp (also known as the seed coat or bran) is the outer covering of the kernel. It consists primarily of relatively coarse cellulosic fiber. The endosperm is the energy reserve for the plant. It contains starch, protein (also known as gluten), and small amounts of relatively fine cellulosic fiber. The distribution of protein and fiber in the endosperm is not uniform. The starch in the endosperm that is in close contact with the protein and fine fiber is commonly known as "hard" starch and this portion of the endosperm is yellow in color. The hard starch, protein, and fine fiber form what is commonly known as a matrix. The starch in the endosperm that is substantially free of the protein and fine fiber is commonly known as "soft" starch and is white in color. The germ (also known as the embryo) is a miniature plant with a root-like portion and several embryonic leaves. The germ also contains oil.

A corn kernel generally contains about 10 to 30 percent water at the time of harvest. In the United States, a water content of about 15 percent is considered standard. On a dry substance basis, a corn kernel contains about 80 percent starch, 12 percent protein, 6 percent oil, and 2 percent fiber. All percentages herein are based on weight unless otherwise noted.

Starch is stored in the kernel in the form of discrete crystalline bodies known as granules. Starch granules have a diameter of about 5 to 25 microns. Starch granules are insoluble in water. However, if the granules are heated in water at a temperature of at least about 125° F. (52° C.), subjected to shear, or subjected to other treatments, they can lose their crystalline structure and form a gel or paste. This process is commonly known as gelatinization or pasting. Once starch has gelatinized or pasted, it can never return to the crystalline granular structure.

On a molecular level, starch is a polymer of anhydroglucose units ($C_6H_{12}O_6$). Starch is a member of the general class of carbohydrates known as polysaccharides. Polysaccharides contain multiple saccharide units, disaccharides contain two saccharide units, and monosaccharides contain a single saccharide unit. The length of a saccharide chain (the number of saccharide units in it) is sometimes described by stating its "degree of polymerization" (abbreviated to D.P.). Starch has a D.P. of 1000 or more. Maltose is a disaccharide (its D.P. is 2) that is composed of two glucose units. Glucose (also known as dextrose) is a monosaccharide (its D.P. is 1). Saccharides having a D.P. of about 5 or less are sometimes referred to as sugars. The solubility of saccharides in water generally increases as the D.P. decreases. The distribution of the varying D.P. sugars in a mixture is frequently expressed as a dextrose equivalent (DE) which is the total reducing power of all the sugars present relative to glucose as 100.

The saccharide units in starch are connected to each other in one of two ways. When connected together in alpha-1,4-linkages, the starch molecule is linear. When connected together in alpha-1,6-linkages, a branch occurs. The relative number of the two linkages varies depending on the variety of corn. Both types of linkages are sometimes referred to as glucosidic linkages. Cellulose is also a polysaccharide formed of glucose units. However, the glucose units in cellulose are connected together in beta-1,4-linkages which cannot be broken down in the human digestive system.

2. Dry Milling Process

A wide variety of processes have been used to separate the various components of corn. These separation processes are commonly known as corn refining. Commercial corn refining processes do not make a precise separation of the components. In other words, each component contains some of one or more of the other components. The cost to make a more precise separation is inevitably outweighed by the economic benefits. One of the earliest processes developed is commonly known as the dry milling process.

In a typical dry milling process, the corn kernels are first cleaned and then soaked in water to increase their moisture content. The softened corn kernels are then ground in coarse mills to break the kernel into three basic types of pieces—pericarp, germ, and endosperm. The pieces are then screened to separate the relatively small pericarp and germ from the relatively large endosperm.

The pericarp and the germ are then separated from each other. The germs are then dried and the oil is removed. The remaining germ is typically used for animal feed. Meanwhile, the endosperm is ground to make corn flakes. The corn flakes contain most of the starch and protein from the kernel.

3. Wet Milling Process

A different process was developed to isolate granular starch from corn. The process is commonly known as the wet milling process. After isolation, the granular starch is processed in one of many different ways. The starch can be dried and sold as unmodified starch. The starch can be modified and used for food or industrial purposes. The starch polymer can be partially shortened to produce corn syrup or shortened all the way to the individual glucose (dextrose) units. The partial shortening process is commonly known as liquefaction because the resulting fragments are water soluble. The process of shortening all the way to glucose is commonly known as saccharification. If shortened all the way to glucose, the glucose molecules can be isomerized to fructose. Fructose is considerably sweeter than glucose and is widely used in the food industry.

In a typical wet milling process, the corn kernels are first cleaned and then soaked for 24 to 48 hours in warm water containing sulfurous acid ($H_2SO_3$). The temperature of the water is generally less than 125° F. (52° C.) so the starch does not gelatinize. The sulfurous acid controls fermentation and also helps in the physical separation of the components that occurs later. This soaking step is commonly known as steeping. During steeping, water soluble proteins and other substances dissolve into the steepwater. These components are then recovered from the steepwater.

After steeping, the softened corn kernels are ground in coarse mills to break the kernel without damaging the germ. The kernels then flow to centrifugal separators which separate the less dense germs from the denser pericarp and endosperm. The germs are then dried and the oil is removed.

The pericarp and endosperm are then ground in fine mills. The finely ground stream flows to screens which separate the small particle size pericarp from the larger particle size endosperm. The endosperm stream then flows to centrifugal separators that separate the less dense protein from the denser starch. The finished starch is in granular form and is suitable for many different types of further processing.

The wet milling process is effective at isolating starch in the granular form. Many commercial processes are able to isolate over 90 percent of the starch in the kernel. In other words, less than 10 percent of the starch ultimately ends up in other components. However, the use of sulfurous acid causes many environmental problems. Furthermore, the process uses large quantities of water and produces large quantities of waste water that must be treated.

4. Enzymes

When the wet milling process was first developed, the corn starch was liquefied and saccharified by treatment with acids at relatively high temperatures and pressures if reduced D.P. products were desired. Within the past few decades, the corn refining industry has largely switched to the use of enzymes instead of acids. An enzyme is a protein formed by living cells that catalyzes a broad spectrum of biochemical reactions. Enzymes are very specific in that they catalyze one particular reaction and no others. The use of enzymes enables liquefaction and saccharification to be conducted at lower temperatures and pressures which, in turn, reduces various undesired reactions of the starch. These undesired reactions reduce the yield of desired products and also produce reaction products that contribute off-colors and flavors.

Enzymes that are commonly used in corn refining include: (1) glucosidic linkage cleaving enzymes that break down the glucosidic linkages in starch; (2) protease enzymes that break down the peptide linkages in protein; and (3) cellulase enzymes that breaks down the beta-1,4-linkages in cellulosic fiber. The most common glucosidic linkage cleaving enzymes are: (1) amylase enzymes that break down the linear alpha-1, 4-linkages and the branched 1-6-linkages in the starch molecule; (2) pullanase enzymes that break down the branched 1,6-linkages only; and (3) maltase enzymes that break down maltose into two glucose molecules. The most common amylase enzymes are: (1) alpha-amylase that is added in the liquefaction step to split the starch molecule into soluble fragments; and (2) glucoamylase (also known as glucohydrolyase or amyloglucosidase) that is added in the saccharification step to break the fragments into glucose. Some of these enzymes are naturally present in the corn (e.g., maltase) while others are added by the refiner.

The activity of enzymes is dependent on temperature, pH, and other factors. For example, an enzyme that has its maximum activity at 65° C. has only about half that activity at 55° C. and at 75° C. To a large extent, enzyme manufacturers have tried to supply enzymes to the corn refining industry that will function at the process conditions. However, the conditions are rarely optimal for the enzymes.

5. Ethanol Processes

Fermentation is a process by which microorganisms such as yeast digest sugars and starches to produce ethanol and carbon dioxide. The basic reaction is

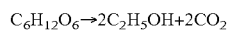

Yeast reproduce aerobically (oxygen is required) but can conduct fermentation anaerobically (without oxygen). The fermented mixture (commonly known as the beer mash) is then distilled to recover the ethanol. Distillation is a process in which a liquid mixture is heated to vaporize the components having the highest vapor pressures (lowest boiling points). The vapors are then condensed to produce a liquid that is enriched in the more volatile compounds.

Various fractions of corn have been used for fermentation, including the entire kernel, just the endosperm, and just the starch. For example, a process based on the dry milling process in which all the components of the kernel are fed to fermentation is illustrated in FIG. 1. A process based on the wet milling process in which granular starch is isolated and then optionally fed to fermentation is illustrated in FIG. 2. Processes have also been disclosed in which the starch is liquefied and saccharified before fermentation.

For example, Keim, U.S. Pat. No. 4,361,651, Nov. 30, 1982, discloses a corn refining process in which the corn is steeped, milled, and degermed. The degermed corn is then liquefied and saccharified. The pericarp and the gluten are then removed and the glucose solution is fermented. The fermented mash is then distilled to recover ethanol. The Keim process is based upon the wet milling process and includes the steeping, milling, and degerming steps. Accordingly, the Keim process suffers from the disadvantages of the wet milling process, including environmental problems caused by the use of sulfurous acid and the production of large quantities of waste water.

As another example, Singh et al., U.S. Pat. No. 6,254,914, Jul. 3, 2001, discloses a corn refining process in which the corn is soaked in hot water (preferably distilled water for 12 hours), milled, and degermed. The pericarp is then removed and the resulting stream containing starch, protein (gluten), and fine fiber is then ground and saccharified. The mixture is then fermented. The fermented mash is then distilled to recover ethanol. The Singh et al. process is relatively slow and it produces large quantities of waste water.

Accordingly, there is a demand for a corn refining process that quickly and efficiently produces ethanol without the use of sulfurous acid and without the production of large quantities of waste water. There is also a demand for a corn refining process that is conducted at optimal conditions for the enzymes. There is further a demand for a corn refining process in which a variety of components can be isolated as economic conditions dictate without changing the basic steps.

SUMMARY OF THE INVENTION

The general object of this invention is to provide an improved process for refining corn. A more particular object is to quickly and efficiently produce ethanol from corn without the use of sulfurous acid, without the addition of nitrogen compounds, and without the production of large quantities of waste water. Another more particular object is to provide a corn refining process that is conducted at optimal conditions for the enzymes. Another more particular object is to provide a corn refining process in which a variety of components can be isolated as economic conditions dictate without changing the basic steps or sacrificing the yield of ethanol.

I have invented a process for refining corn. The process comprises: (a) providing corn kernels having a moisture content of about 10 to 30 percent and comprising: (i) a pericarp comprising coarse fiber; (ii) an endosperm comprising soft starch, hard starch, protein, and fine fiber; and (iii) a germ; (b) steeping the corn kernels in recycled water from downstream processes, which water has a temperature of about 125 to 160° F., is essentially free of sulfurous acid and contains effective amounts of amylase enzymes, in a counter-current steeping reactor for about 10 to 20 hours to produce an aqueous slurry of steeped corn kernels having a moisture content of about 40 to 50 percent; (c) coarsely grinding the steeped corn kernels to produce a coarsely ground stream comprising coarse fiber, soft starch, hard starch-protein-fine fiber fragments, and germs; (d) heating the coarsely ground stream in the presence of effective amounts of amylase enzymes to gelatinize starch clinging to the coarse fiber and germs and to produce a partially gelatinized stream; (e) subjecting the partially gelatinized stream to sufficient shear and cavitation forces in the presence of effective amounts of amylase enzymes to gelatinize substantially all the starch and to produce a liquefied stream; (f) exposing the liquefied stream to effective amounts of amylase enzymes to produce a saccharified stream; (g) adding an effective amount of yeast to the saccharified stream and fermenting it to produce carbon dioxide and a fermented stream containing ethanol; (h) removing the carbon dioxide produced during fermentation and recycling some for gas lift agitation and blanketing; and (i) distilling the fermented stream to produce an ethanol stream and a bottoms stream.

The process of this invention quickly and efficiently produce ethanol from corn without the use of sulfurous acid, without the addition of nitrogen compounds, and without the production of large quantities of waste water. The process uses smaller quantities of enzymes than conventional processes because it is conducted at optimal conditions for the enzymes, because enzymes are in contact with the corn throughout the process, and because of the shear and cavitation forces in the homogenizer supplement the action of the enzymes. The process enables the isolation of a variety of components as economic conditions dictate without changing the basic steps.

DETAILED DESCRIPTION OF THE INVENTION

1. The Invention in General

Figure 1:
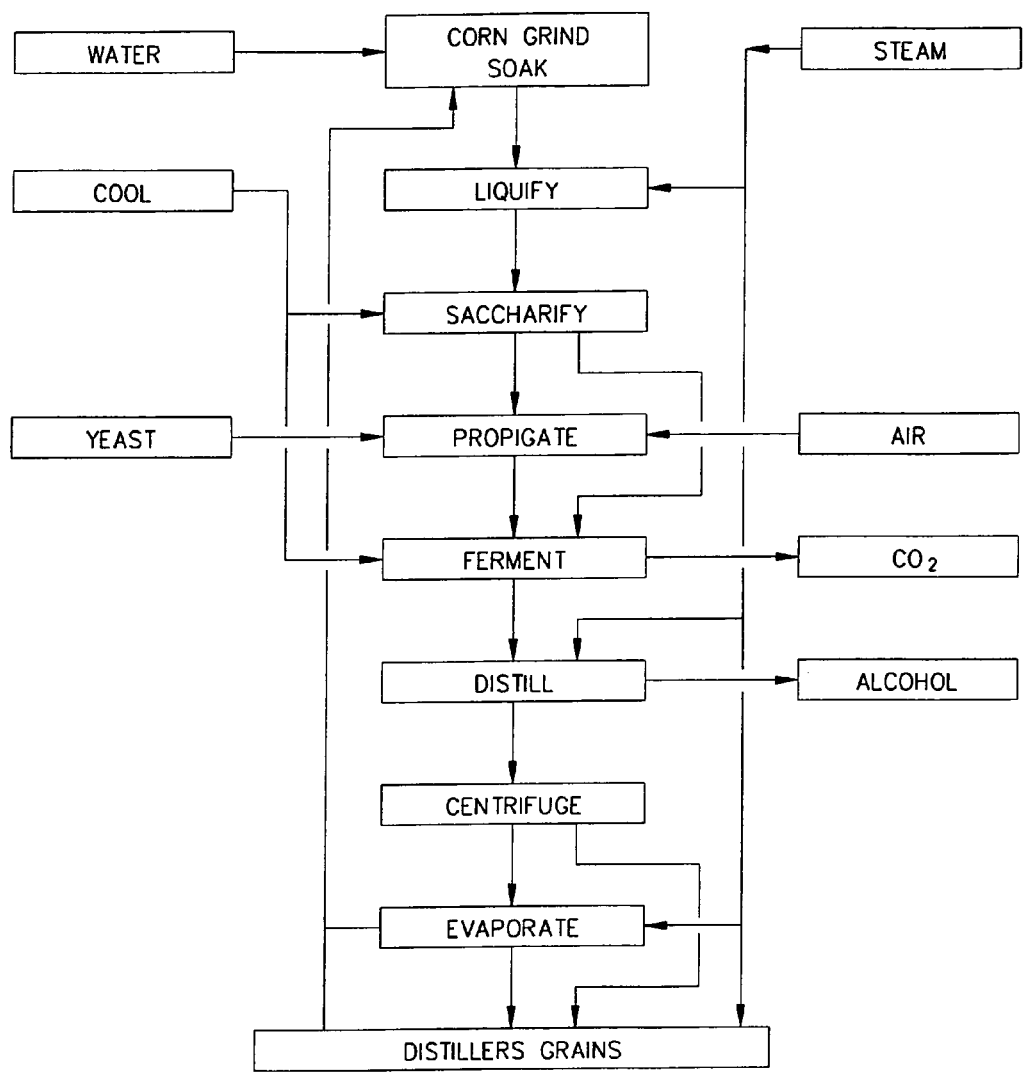
FIG. 1 is a schematic diagram of a prior art corn refining process for ethanol production based on a conventional dry milling process.
Figure 2:
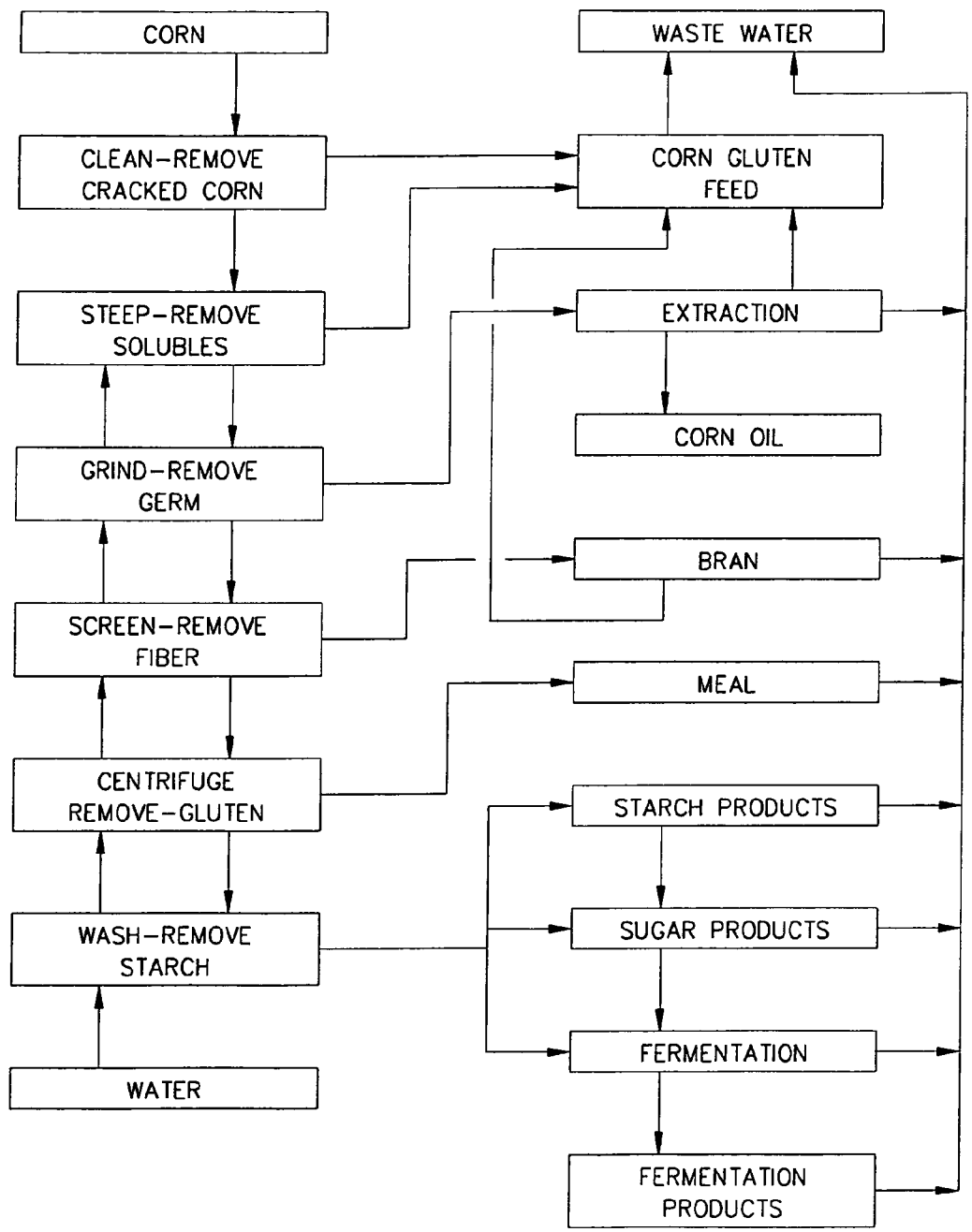
FIG. 2 is a schematic diagram of a prior art corn refining process for ethanol production based on a conventional wet milling process.
Figure 3:
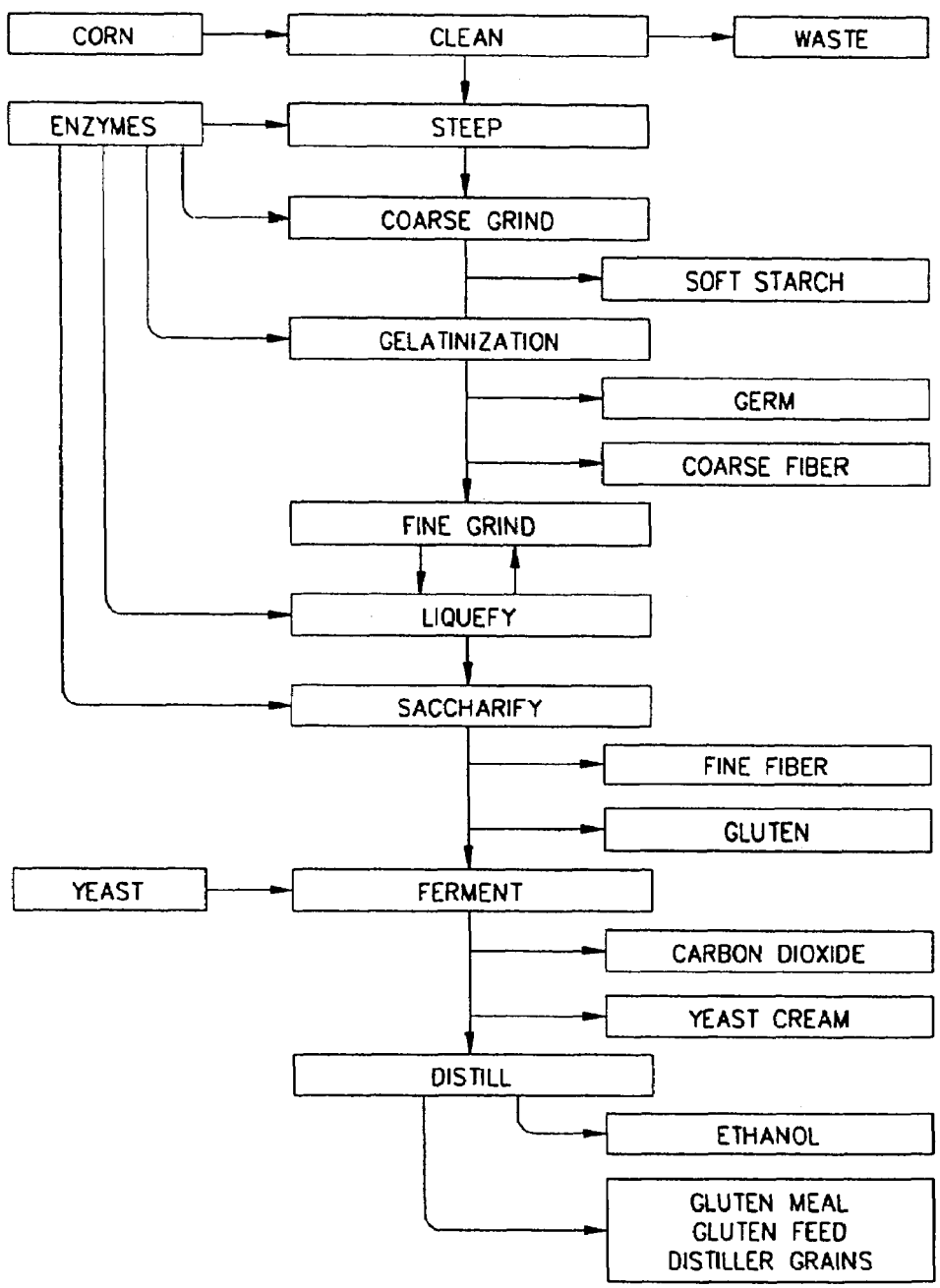
FIG. 3 is a simplified schematic diagram of the overall corn refining process of this invention.
Figure 4:
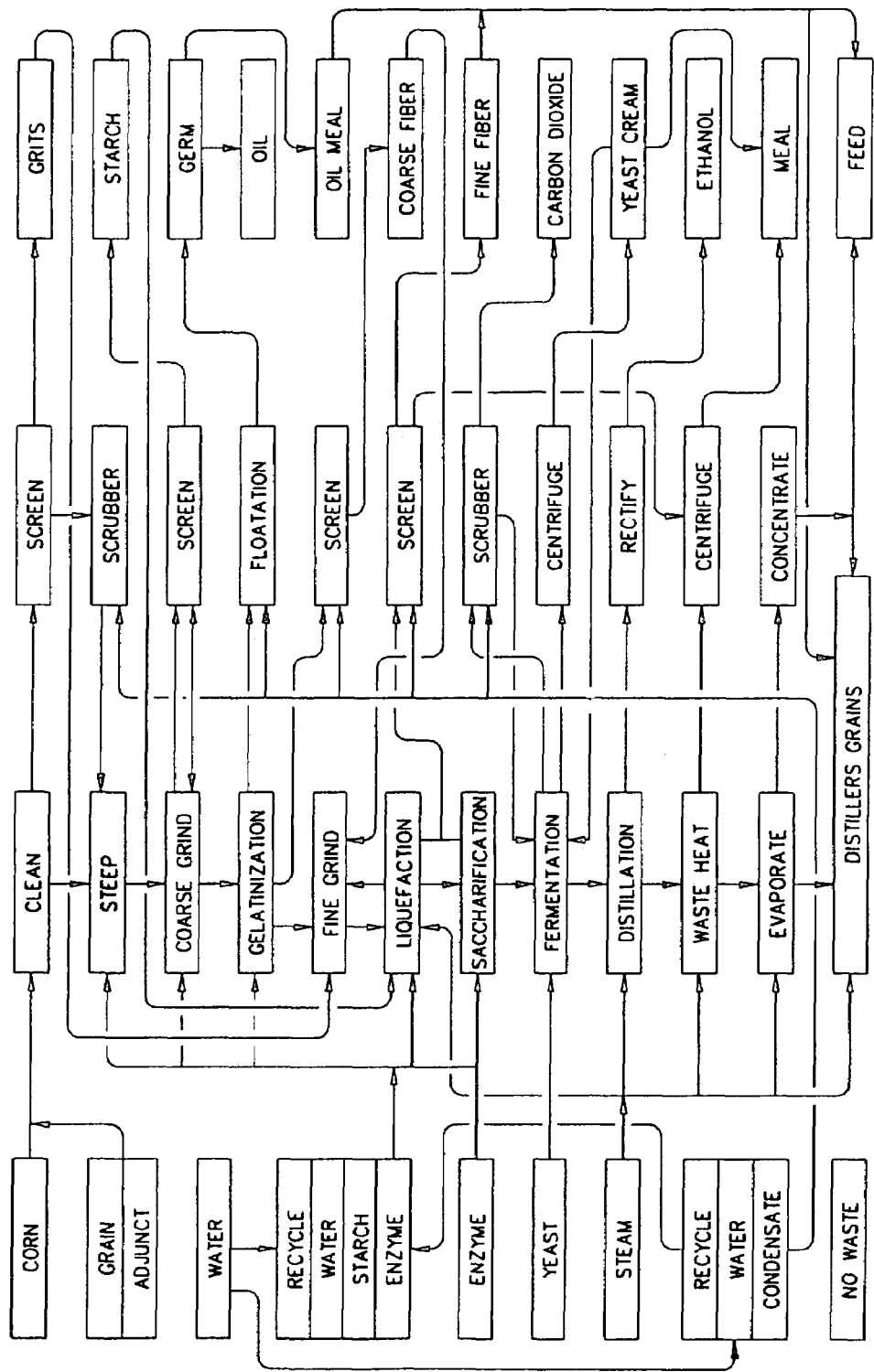
FIG. 4 is a more detailed schematic diagram of the overall process.

The process of this invention refines corn. The process separates the various corn fractions and chemically converts the starch to glucose and the glucose to ethanol. The overall process is illustrated in simplified form in FIG. 3. Omitted for clarity are water and steam, two important raw materials for the process. Also omitted for clarity are recycle lines, separations, minor by-product lines, etc. FIG. 4 illustrates the overall process in more detail. The stream containing the starch (and later containing the starch derivatives glucose and ethanol) is considered the primary stream because of its size and economic importance. Various corn components are optionally isolated (removed from the primary stream) at different steps of the process. In general, it is preferred to isolate these components for a variety of reasons, including the fact that the quality and nutritional value of the components deteriorate as the processing continues. These isolated components are suitable for a wide variety of conventional corn refining products, including distillers grains with solubles (DGS), corn grits, starch media, corn oil, coarse fiber (bran), fine fiber, germ oil meal, gluten meal, gluten concentrate (steepwater concentrate), and gluten feed. By-products include carbon dioxide and yeast cream. The individual steps of the process are discussed in detail below.

2. Suitable Grains

A variety of grains with a starch component are advantageously refined with the process of this invention. Suitable grains include corn, rice, oats, sago, barley, canola, cassava, Jerusalem artichokes, mustard seed, flax, fava beans, lentils, milo, peas, rye, safflower, soybeans, sunflower seeds, tricale, wheat, and the like. The preferred grain is corn because of its large starch component and its abundant commercial availability. The preferred corn is United States grade no. 2 yellow dent corn. For convenience, most descriptions of the process herein refer only to the use of corn as the raw material.

3. Cleaning

The first step of the process is to clean the corn, i.e., to separate whole corn kernels from all other matter. Cleaning is preferably performed by passing the corn over or through a series of three varying sized screens. Particles larger than a corn kernel (commonly known as the scalps and consisting of cobs, stalks, dirt, metal, and other extraneous material) are retained on the largest screen and are discarded as waste. Whole corn kernels (and some cob and stalk fragments having the same size as whole corn kernels) are retained on the next largest screen. The whole corn kernels (and other material of the same size) are fed to the steeping reactor described below.

Cracked or broken corn kernels (commonly known as grits) are retained on the next largest screen. These particles are preferably removed because they do not separate downstream in the same way as whole kernels. They are preferably added back to the primary stream just prior to the fine grinding/liquefaction step. In prior art processes, the grits are typically removed and sold as corn grits or are added to the gluten feed. Adding the grits back into the primary stream increases the yield of starch derivatives. The very smallest particles that pass through the third and finest screen are aspirated. The aspirated corn dust is preferably contacted with recycled steep water in a scrubber, heated to reduce bacteria, and then fed to the steeping reactor. The non-aspirated materials such as sand and soil grit are discarded. The moisture content of the corn is typically about 10 to 30 percent, but is not critical.

4. Steeping

The next major step of the process is to steep the cleaned corn kernels in water that is essentially free of sulfurous acid.

Figure 5:
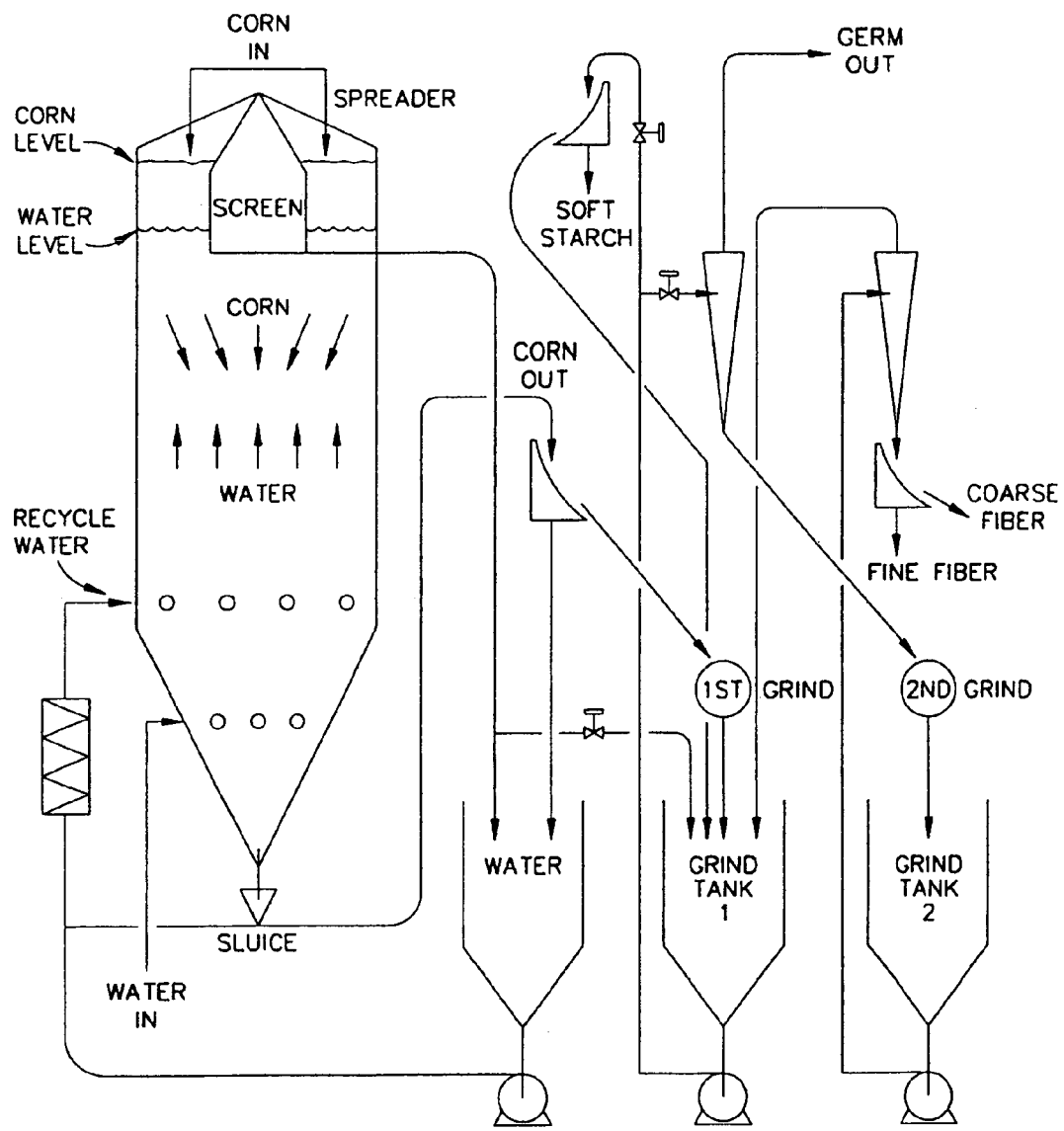
FIG. 5 is a schematic diagram of the steeping and coarse grinding steps of the process.

The preferred steeping step is illustrated in FIG. 5 which uses symbols for processing equipment that are well known in the art. Steeping the corn kernels causes physical changes in the various components that facilitates subsequent separations.

The corn kernels and water are added to a steeping reactor. Unlike conventional processes, all the water is preferably recycled from downstream processes and preferably contains effective amounts of at least three different types of enzymes: (1) an amylase enzyme; (2) a protease enzyme; and (3) a cellulase enzyme. The recycled water preferably contains two different types of amylase enzymes: (1) an alpha-amylase; and (2) a glucoamylase. The recycled water may also contain other glucosidic linkage cleaving enzymes such as pullanase and maltase. The presence of the enzymes in the steeping reactor enables the breakdown of the starch and other components to begin at a much earlier stage than conventional processes. The level of the enzymes in the steeping reactor is monitored and make-up enzymes are added as needed. The term "effective amount" is used herein to mean that the enzymes are present in sufficient quantity to produce a measurable effect on the corn. In general, the amounts of the enzymes are so small that they are not measured directly. Instead, the enzymes are added in a quantity to achieve the desired effect on the corn. The recycled water also contains small amounts of yeast, acetic acid, lactic acid, and other materials from downstream steps.

The water generally has a pH of about 3.8 to 6.5. The water has a temperature of about 125 to 160° F. (52 to 71° C.), preferably about 140 to 155° F. (60 to 68° C.), and most preferably about 145 to 150° F. (63 to 66° C.). This temperature is greater than in conventional processes because the recovery of granular starch is not a goal so a slight amount of gelatinization during steeping is not objectionable. The water slurry in the reactor generally has a solids (dry substance) level of about 9 to 14 percent. This combination of pH, relatively high temperature, and dry substance level enables the enzymes to function optimally. The conditions also retard yeast fermentation and objectionable microorganism growth. Thus, the conditions make the addition of sulfurous acid unnecessary. Accordingly, the water preferably contains essentially no sulfurous acid (i.e., no more than a negligible amount) because sulfurous acid is an environmental problem and causes corrosion of equipment. The water is generally added to the steeping reactor at the rate of about two to three gallons per minute per square foot of cross-sectional area of the steeping reactor. This rate of addition exceeds the rate at which water leaves the reactor with the steeped corn kernels. The excess is used for increasing the moisture content of the corn and for extracting the steepwater solubles. The amount of water in the steepwater reactor relative to the amount of corn affects the osmotic pressure which, in turn, affects bacteria growth and the movement of solubles through the pericarp.

The steeping is preferably conducted in a continuous counter-current reactor as shown in FIG. 5. The reactor is a vertical cylinder with a cone at its bottom. It is similar in structure to the steeping reactor disclosed in Randall et al. U.S. Pat. No. 4,106,487, issued Aug. 15, 1978. The kernels are added at the top and evenly distributed across the surface area. The kernels then move downward through the water in plug flow by the force of gravity. The lightweight materials added with the whole corn kernels (cobs, stalks, etc.) are trapped with the whole corn kernels and move along with them down the reactor. A center collector at the top of the steeping reactor collects water for recycle and steepwater solids blow down. The center collector is continuously cleaned by the moving corn. The moving corn acts as a filter media and traps materials that might choke the corn screen.

The steepwater collected at the screen on the top of the reactor is heated to kill any objectionable bacteria flushed from the reactor or added from downstream processing and also to maintain the temperature of the reactor. The water is added on the side of the reactor just above the top of the cone to expand the plug flow mass of corn to facilitate removal of the corn as a slurry at the bottom of the cone. Fresh water is distributed in the cone to maintain the counter-current washing of the corn.

The kernels are generally soaked in the water for about 10 to 20 hours, preferably about 12 to 16 hours, to produce corn kernels having a moisture content of about 40 to 50 percent, preferably about 45 percent. The kernels are removed from the bottom of the reactor as an aqueous slurry. A regulating orifice is used to control the rate at which the kernels and water are removed. The slurry is preferably passed through a screen to reduce the amount of water in the slurry before it flows downstream for coarse grinding.

5. Coarse Grind

The next step of the process is to coarsely grind the steeped kernels to break them apart into four different types of fragments—pericarp (coarse fiber), soft starch (containing over 99 percent starch), hard starch in a matrix with protein and fine fiber, and germ. A preferred coarse grinding step is illustrated in FIG. 5 in which the steeped kernels are mixed with steepwater blowdown from the steep reactor and are then ground sequentially in two coarse grinding mills (identified as first grind and second grind). As mentioned above, the steepwater contains recycled cellulase enzymes. The addition of new cellulase enzymes is preferably made at the coarse grinding step. A preferred coarse grinding mill is a cage mill containing cage pins and breaker plates. An especially preferred cage mill is a Stedman cage mill, a commercial product of Stedman Machine Company of Aurora, Ind. The soft starch fragments are generally smaller (less than 40 microns) than the other types of particles and the germs are less dense than the other types of products. These physical characteristics enable separations to be made downstream if desired.

6. Soft Starch Removal

After the coarse grinding, the soft starch particles are optionally removed. If recovery of this soft starch is desired, the ground particles from the coarse grind are screened to separate the soft starch from the other particles. As mentioned above, the soft starch recovered by this step is relatively pure in that it typically contains less than about one percent protein and fine fiber. The soft starch can be used in many ways, including as a growth media for the yeast that is used downstream in the process.

7. Partial Gelatinization

The next step of the process is to partially gelatinize the starch present in the primary stream. Partial gelatinization is performed by heating the coarsely ground stream, whether or not the soft starch particles have been removed, to a temperature of about 150 to 180° F. (66 to 82° C.) in the presence of an effective amount of amylase enzymes. Some of the amylase enzyme is present in the recycled water forming the primary stream and, if desired, some can be added fresh to the primary stream at this point in the process. A preferred amylase enzyme is a low temperature alpha-amylase enzyme. An especially preferred enzyme is GENENCOR VISCOAT alpha-amylase enzyme derived from a genetically modified strain of *Bacillus amyloliquifaciens*, a commercial product of Genencor International, Inc. of Rochester, N.Y.

This step is known as "partial" gelatinization because the combination of heat and enzymes gelatinizes some or all the starch clinging to the germ and coarse fiber, but gelatinizes little or none of the other starch in the stream, namely, the starch in the hard starch fragments. Gelatinizing the starch on the germ and coarse fiber makes it water soluble and enables it to be recovered if the germ and coarse fiber are removed downstream and washed with water. Without this partial gelatinization, much of the insoluble starch clinging to the germ and coarse fiber is not removed by washing and winds up with other products. This step is also known as cooking or as preliminary liquefaction because the gelatinized starch becomes liquefied (water soluble).

8. Germ Removal

After partial gelatinization, the germs are optionally removed. Germ removal is conventional. If recovery of the germs is desired, the partially gelatinized stream is dewatered to about 15 to 17 percent solids. At this level, the germs float while the other components sink. The slurry stream then flows to a centrifugal separator to separate the germs from the other components. The germs are then dewatered and washed to remove residual starch and protein. The washwater is preferably returned to the steeping reactor. The germs are then typically processed to remove the oil. The remaining solid material is typically sold as corn oil meal or is added with other components and sold as corn meal, corn feed, distillers grain with solubles, etc.

9. Coarse Fiber Removal

After the removal of the germ, the insoluble coarse fiber from the pericarp is optionally removed. If recovery of the coarse fiber is desired, the stream is preferably screened. The larger coarse fiber particles are retained on a suitably sized screen while the smaller starch-protein-fine fiber particles pass through. Alternatively, the coarse fiber can be removed by the process described in Singh et al., U.S. Pat. No. 6,254,914, Jul. 3, 2001. The coarse fiber is then dewatered and washed. The coarse fiber is then dried or conditioned as desired. It can then be steam exploded, expanded, chemically treated, treated with cellulase enzymes, and/or processed in other ways. The fiber can be used for fermentation (if expanded) or to produce pectin, cellulose, lignin, mannose, xylose, arabinose, galactose, galacturonic acid, and other materials.

10. Liquefaction with Simultaneous Fine Grind

Figure 6:
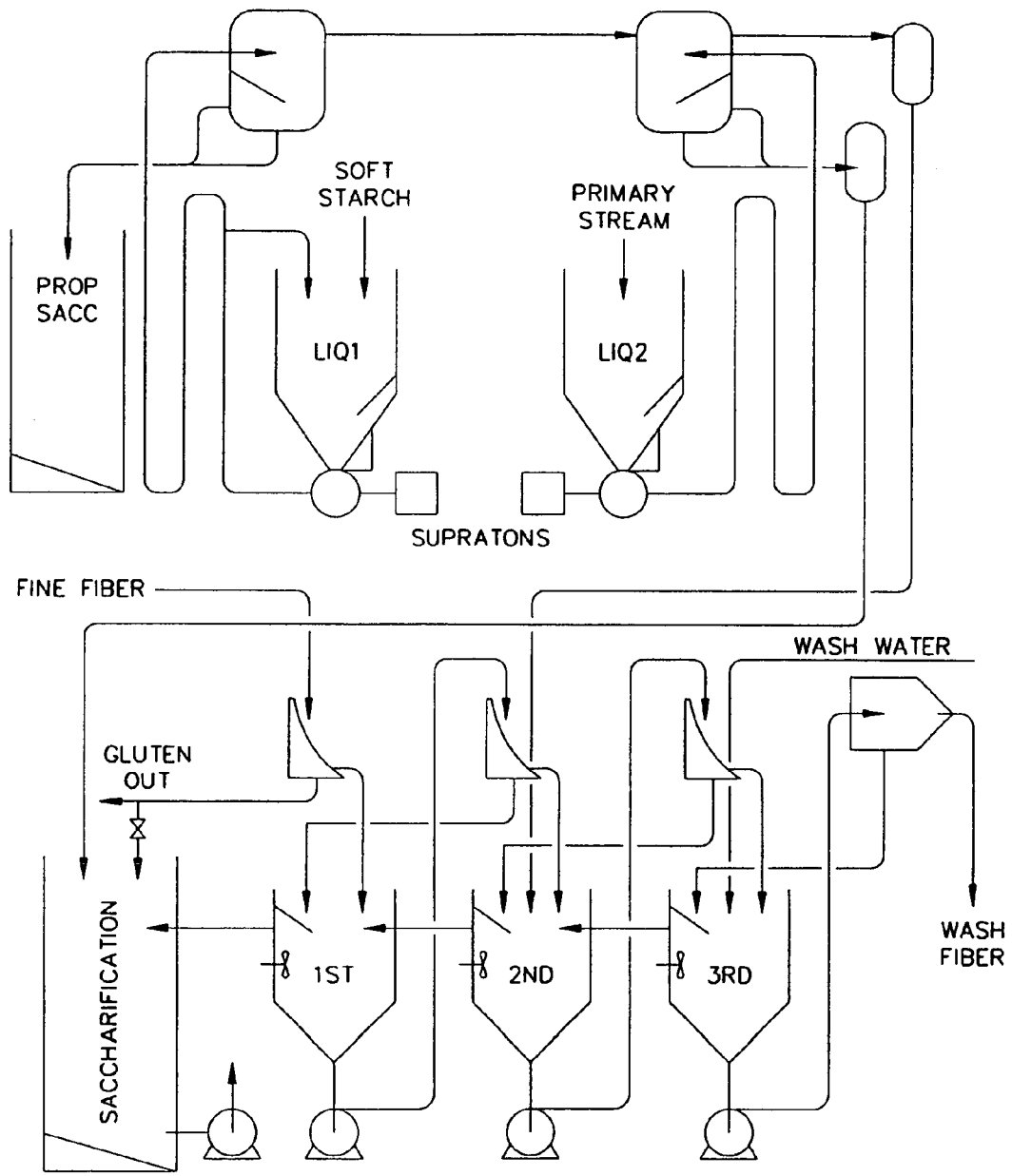
FIG. 6 is a schematic diagram of the liquefaction step thereof.

The next step of the process is to finely grind and liquefy the primary stream. These two procedures are preferably performed simultaneously and are therefore considered a single step. This single step is referred to herein as liquefaction even though it is understood that a separate fine grind is sometimes performed. The liquefaction step is illustrated in FIG. 6. At this point in the process, the primary stream consists primarily of a slurry of starch granules, protein, and fine fiber. The primary stream may also contain one or more of the materials optionally removed upstream (soft starch, coarse fiber, and germ). The cracked and broken corn kernels (grits) from the upstream cleaning step are preferably added to the primary stream at this point to recover the starch present. The liquefaction step gelatinizes all the starch granules, breaks the starch down into smaller fragments, and makes the starch more accessible for downstream processing. The liquefaction step also helps to loosen any residual starch from the other components and reduces the size of the protein particles.

Before liquefaction, a variety of liquid streams are preferably added to the primary stream. In particular, waste streams from any upstream washing of the germ and the coarse fiber, and from the downstream washing of the protein and starch, are added. The stream is then preferably adjusted to about 36 to 42 percent solids, most preferably about 38 to 40 percent solids. In contrast, prior art processes typically perform liquefaction at less than 35 percent solids. Effective amounts of amylase are present during liquefaction. Some of the amylase enzyme is present in the recycled water and some is preferably added fresh to the primary stream at this point in the process. An especially preferred amylase is GENENCOR VISCOAT alpha-amylase enzyme derived from a genetically modified strain of *Bacillus amyloliquifaciens*, a commercial product of Genencor International, Inc. of Rochester, N.Y. The amylase enzymes reduce the length (D.P.) of the starch fragments generated during liquefaction. The cellulase and protease enzymes break down the cellulosic fine fiber/protein matrix which, in turn, helps to free the starch.

Figure 7:
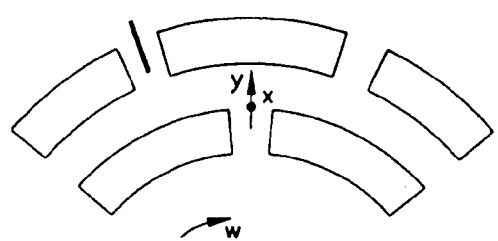
FIG. 7 is a top plan view of a liquefaction apparatus.
Figure 8:
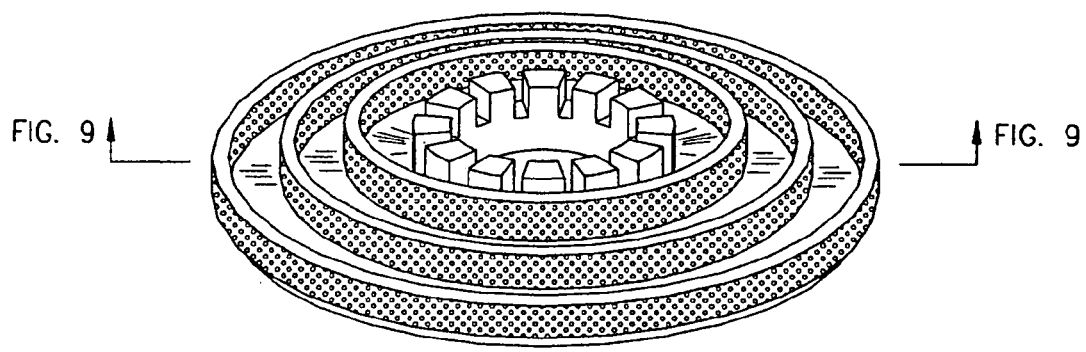
FIG. 8 is a perspective view of a liquefaction apparatus.
Figure 9:
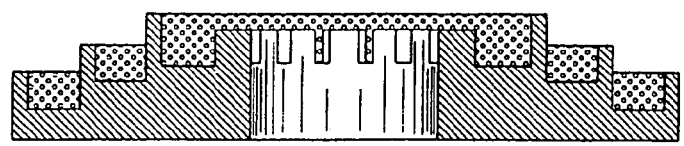
FIG. 9 is a sectional side elevation view of a liquefaction apparatus.

The liquefaction is preferably performed in a rotary homogenizer. Suitable rotary homogenizers include the DISPAX machine, a commercial product of Ika-Works, Inc. of Cincinnati, Ohio, and the SUPRATON machine, a commercial product of BWS Technologie, GmbH of Germany and marketed in the U.S.A. by Centrisys, Inc. of Kenosha, Wis. The most preferred rotary homogenizer is the SUPRATON machine. The machine is a rotor-stator machine having concentric tool rings that are radial slotted and/or drilled to provide intermeshing radial surfaces. It is illustrated in FIGS. 7, 8, and 9. The slurry is pumped under pressure into a chamber and is then forced laterally. The slurry passes through the gaps as the rotor spins past the gaps in the stator. Flow is most pronounced when the gaps in the rotor align with the gaps in the stator. The result is a pulsing flow with a rapid succession of compressive and decompressive forces.

The rotary homogenizer thus subjects the slurry to shear and cavitation forces. More particularly, the slurry is subjected to multi-stage hydrodynamic high shear, high-frequency oscillating forces, intensive micro-volume mixing, and pressure increases. The repeated compression and decompression create microcavities that are believed to burst the granules from the inside. Accordingly, treatment in a rotary homogenizer produces unique changes in the starch granule. While conventional grinding generally cuts the starch granules perpendicular to its longitudinal axis to produce more spherical particles that remain in the granular ungelatinized form, treatment in a rotary homogenizer produces smaller, more irregularly shaped particles containing gelatinized starch. The starch in these particles is more completely liquefied with a significantly reduced viscosity requiring less reaction hold time at the elevated temperature which, in turn, increases the half life of the enzymes. Accordingly, the starch in these particles is easier to saccharify.

As illustrated in FIG. 6, a preferred liquefaction step is to treat the primary stream and the soft starch previously removed in two parallel SUPRATON rotary homogenizers. The liquefaction is generally performed at temperatures less than 212° F. (100° C.), preferably about 150 to 200° F. (66 to 93° C.), and most preferably about 155 to 170° F. (68 to 77° C.) depending on the optimum activity of the amylase enzyme used. These temperatures are much less than the typical temperatures for liquefaction in prior art processes.

Lower temperatures mean less heating is required prior to liquefaction and less cooling is needed after liquefaction. The liquefaction is generally performed with an enzyme level of only about 0.01 to 0.015 percent, considerably lower than in prior art processes. As previously discussed, the use of a rotary homogenizer enables the liquefaction and fine grind to be conducted simultaneously. The use of a rotary homogenizer enables streams having a solids level of up to about 40 percent to be processed and produces a liquefied stream having a relatively low viscosity, generally less than about 20,000 centipoises and preferably less than about 10,000 centipoises. In contrast, conventional processes produce a stream having a viscosity of at least about 80,000 centipoises prior to saccharification.

11. Saccharification

The next step of the process is to cool and saccharify the starch fragments in the primary stream. Saccharification is the process by which the linkages between the individual saccharide units in the fragments are broken by treatment with an effective amount of a glucosidic linkage cleaving agent. Saccharification increases the DE of the primary stream by converting the polysaccharide fragments into lower D.P. products including glucose. Preferred glucosidic linkage cleaving agents include amylase enzymes such as alpha-amylase and glucoamylase. Other agents include pullanase and maltase. It is most preferred to add fresh glucoamylase at this step.

Saccharification is generally performed in a continuous cascade reactor, but can also be performed in batch tanks or a combination of the two. At the same time glucosidic linkage cleaving agents are added, an effective amount of protease enzymes is preferably added. The protease enzymes break down the peptide linkages in the protein and help to convert the protein to a form that is available for the yeast. The converted protein provides the nitrogen necessary for the yeast during fermentation. Alternatively, the protease enzymes can be added during fermentation. The saccharification is generally conducted at a temperature of about 135 to 145° F. (57 to 63° C.).

The DE of the saccharified stream is a function of the residence time, the enzyme level and activity, and other factors. The residence time is generally at least about 10 hours. To raise the DE to about 36 to 40 with a viscosity of about 100 centipoises, a residence time of about 12 to 14 hours is generally required. To raise the DE above about 90, a residence time of 30 to 40 hours is generally required.

12. Fine Fiber Removal

After saccharification, the larger pieces of insoluble fine fiber are optionally removed. If recovery of the fine fiber is desired, the saccharified stream is preferably screened. Most of the fine fiber is larger than the other components and is retained on a suitably sized screen. The fine fiber is then washed by conventional countercurrent screening methods and dewatered in a decanter centrifuge. The centrate is recycled. A preferred centrifuge is a CENTRISYS decanter, a commercial product of Centrisys, Inc. of Kenosha, Wis. After centrifugation, the fine fiber generally contains about 45 to 55 percent solids and less than about 2 percent starch. The fine fiber can be used for human dietary fiber, oil and sugar extraction, alcohol fermentation, animal feed blends, or can be blended with other products.

13. Protein Removal

After saccharification, the insoluble protein (gluten) is also optionally removed. If the fine fiber is removed by screening after saccharification as described in the preceding section, the protein is contained in the screen underflow and is advantageously removed by centrifugation. A centrifuge commonly known as a primary gluten centrifuge is used to remove and wash the protein. Fermentation backset water is preferably used as wash water. The diluted protein is contained in the overflow and the underflow is sent to fermentation. The overflow from the primary gluten centrifuge is fed to a second centrifuge commonly known as a gluten thickener. The protein is thickened to about 18 to 20 percent solids and then fed to a decanter centrifuge, a rotary vacuum filter, or the like where it is thickened to about 45 to 50 percent solids. A preferred centrifuge is a CENTRISYS decanter, a commercial product of Centrisys, Inc. of Kenosha, Wis. The dewatered protein is then dried and sold as corn gluten meal or added with other components and sold as a protein supplement for poultry, swine, fish, and the like.

14. Fermentation

The next step of the process is to ferment the primary stream which contains glucose, disaccharides, and low D.P. polysaccharides and which optionally contains any other components not previously removed. The primary stream also contains various enzymes and it is preferred to add fresh protease enzymes at this step of the process. Simultaneously with the fermentation, the disaccharides and low D.P. polysaccharides are saccharified to glucose. Fermentation converts the glucose molecules into ethanol and carbon dioxide by the action of yeast. The optimal temperature for yeast is less than the optimal temperature for the enzymes used during saccharification. Accordingly, cooling of the primary stream prior to and/or during fermentation is preferred. The preferred temperature for fermentation is about 90 to 95° F. (32 to 35° C.) and most preferably about 92 to 93° F. (33 to 34° C.). The pH is preferably about 3.8 to 4.4, and most preferably about 4.0.

Figure 10:
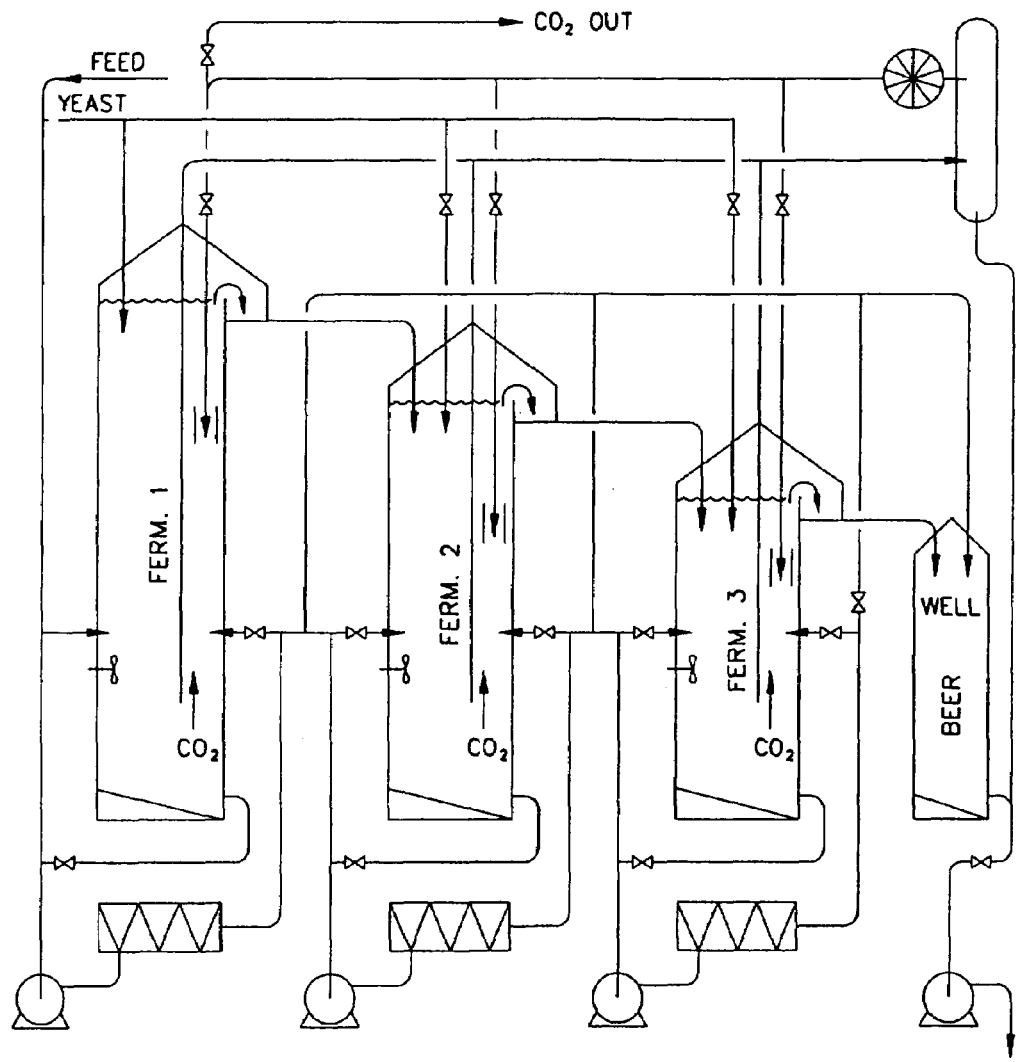
FIG. 10 is a schematic diagram of the fermentation step of the process.

Fermentation is preferably conducted in a continuous cascade integrated reactor as illustrated in FIG. 10. It can also be operated as a batch system for start-ups, clean-ups, and shut-downs. If the soft starch, germ, coarse fiber, fine fiber, and insoluble protein have been previously removed, the fermenter is operated with all the advantages of a clean starch fermentation system. These advantages include improved cooling efficiency with less fouling of heat exchangers, improved agitation with reduced bacterial propagation and contamination. Another benefit from previously removing these components is that the primary stream is reduced by about 10 to 20 percent and the size of the fermentation reactor is reduced accordingly.

As the fermentation takes place, carbon dioxide gas is continuously produced. The gaseous carbon dioxide is recovered, scrubbed with water to recover any entrained alcohol, and then some is recycled to provide agitation to the mash and to blanket the fermentation reactor. The carbon dioxide blanket and agitation limit the oxygen available during fermentation and reduce losses caused by wild and flocculating yeast and by aerobic bacteria such as various species of *Lactobacillus* and *Acetobacter*. Wild yeast and aerobic bacteria transform glucose into unwanted products, including acetic acid, lactic acid, and malodorous compounds, and reduce the glucose available for production of ethanol by the desirable yeast. The losses due to aerobic bacteria are so small that the addition of bactericides (agents that kill bacteria) or bacteriostats (agents that retard the growth of bacteria) during fermentation is not necessary.

Unlike conventional processes, the primary stream contains sufficient amounts of soluble nitrogen compounds from the action of the protease enzymes to enable the yeast to sufficiently propagate. The protease enzymes are added upstream or are added during fermentation. Therefore, there is no need to add nitrogen compounds such as anhydrous ammonia. Accordingly, fermentation is preferably is conducted with essentially no addition of nitrogen compounds. Eliminating the need for adding anhydrous ammonia provides several benefits, including the reduction of cost and the release of nitrogen contaminants to the environment.

The achievable ethanol content is dependent upon the yeast because glucose levels in the feed are easily increased. Current yeast strains can achieve ethanol contents of about 18 to 20 percent. The fermentation is preferably conducted to minimize the foaming resulting from the generation of carbon dioxide. Controlling the solids level (which affects osmotic pressure) and restricting the DE helps to eliminate the need for anti-foaming additives. Any overflow foam is scrubbed and returned to fermentation.

15. Carbon Dioxide Removal

As described above, carbon dioxide gas is continuously produced during fermentation. Some of the carbon dioxide is continuously recycled to provide gas lift agitation to the mash and to blanket the fermentation reactor. Carbon dioxide not recycled is preferably fed to a carbon dioxide refiner.

16. Yeast Removal

After fermentation produces the desired level of ethanol, the fermented mash is withdrawn. The yeast is removed in a centrifugal separator and then adjusted to a solids level of about 15 percent and preserved with propionic acid using conventional methods. A portion of the yeast is then preferably recycled and the remainder is used for the production of yeast cream or is blended with one of the products such as corn gluten meal. If recycled, the yeast is preferably propagated by exposing it to air in the presence of suitable growth media. As mentioned above, the soft starch optionally removed upstream is an excellent growth media for yeast.

17. Distillation and Ethanol Recovery

After fermentation and yeast removal, the beer mash (the primary stream) is distilled. The mash contains ethanol, water, and any other components not previously removed. The ethanol in the primary stream has a higher vapor pressure (lower boiling point) than the other components. Distillation enables the ethanol to be concentrated and recovered in the distillate stream. The distillation is conducted using conventional equipment. The ethanol recovered from the distillation has many uses. For example, it can be used for alcoholic beverages, for fuel, and for industrial uses.

If the germ, coarse fiber, fine fiber, and insoluble protein were removed prior to fermentation, various advantages are realized during distillation. For example, packed columns are suitable in addition to the conventional multiple tray columns, distillation equipment can be sized smaller, fouling of heat exchangers is reduced, mechanical recompression evaporators can be used without the use of additional steam, the solids level can be increased, sufficiently low viscosity is achieved at lower temperatures which improves the quality of the protein concentrate, etc.

18. Subsequent Processing of Distillation Bottoms

The bottoms from the distillation contain small amounts of protein and fine fiber, as well as any other components not removed upstream. The bottoms are generally centrifuged to concentrate the solid materials. A preferred centrifuge is a CENTRISYS decanter, a commercial product of Centrisys, Inc. of Kenosha, Wis. This centrifuge typically produces materials having about 36 to 38 percent solids. The solids are dried if an even lower water content is desired. The solids are commonly sold as distillers grains. The centrate from the centrifuge is, in turn, typically evaporated in a multiple effect forced circulation evaporator to produce a product having about 45 to 50 percent solids. The product can then be dried to about 88 to 90 percent solids. The concentrated and dried centrate is sometimes added to the centrifuge solids and sold as distillers grain with solubles. The condensed salute from the evaporation of the centrate are generally added with other components and sold as gluten concentrate (steepwater solids) or gluten corn feed.

19. Water and Steam

The process of this invention includes the recycle of water for several reasons. Recycling water eliminates the discharge of wastewater from the process which, in turn, eliminates the need for water treatment and reduces environmental pollution. Recycling water also reduces costs and improves efficiencies because low levels of solids can be reclaimed and the recycled water contains enzymes, soluble products, and heat.

The process of this invention also efficiently uses steam heat. High temperature, high pressure steam is used for distillation while lower temperature, lower pressure steam is sufficient for the heating at the upstream steps including steeping, partial gelatinization, and liquefaction steps. Condensate is recovered, used to heat other streams, and then added to the recycled water.

20. Advantages

The process of this invention provides four major advantages over prior art corn refining processes. First, the process produces ethanol from corn without the use of sulfurous acid. Accordingly, hazardous and/or malodorous sulfur compounds are not released into the environment.

Second, liquefaction with a rotary homogenizer provides simultaneous fine grinding. It also enables a much higher solids level (i.e., a reduced volume) and lower viscosity. Less steam, chemicals, enzymes, and process equipment are required because of the reduced volume. Higher sugar levels can be fed to the fermenter providing for higher ethanol concentrations as yeasts are developed.

Third, the process is generally conducted without the addition of ammonia or other nitrogen compounds for yeast propagation because sufficient nitrogen is made available by the action of protease enzymes on the protein in the corn. Accordingly, hazardous and/or malodorous nitrogen compounds are not released into the environment.

Fourth, using recycled carbon dioxide for blanketing and gas lift agitation in the fermentation reactor reduces the fermentation losses caused by wild yeast and by bacteria such as species of *Lactobacillus* and *Acetobacter*.

The process provides many additional advantages as well. For example, it produces greater amounts of ethanol per quantity of corn because the loss of starch in the products is reduced by the continuous availability of cellulase and other enzymes and also because grits are returned to the primary stream.

The process produces little or no waste water.

The process produces little or no air pollution because particulates and odors are scrubbed with recycled water which is then added back to the process.

The process uses smaller quantities of enzymes than conventional processes because it is conducted at optimal conditions for the enzymes and because enzymes are in contact with the corn throughout the process.

The process enables the isolation of a variety of components as economic conditions dictate without changing the basic steps. In other words, the basic process can be conducted with or without the removal from the primary stream of such components as soft starch, germ, coarse fiber, and fine fiber.

The process can use corn having a moisture content as high as about 30 percent with no changes in the process required.

The process is preferably carried out continuously rather than in batch form. Continuous processing is faster and more efficient. It also produces products of greater quality and uniformity.

The process usually does not require the addition of various chemicals during fermentation. Chemicals that are typically added in prior art processes, but are not required in the process of this invention, include bactericides, bacteriostats, and antifoaming agents.

The process is carried out at reduced maximum temperatures and holding times which improves the color and digestibilities of the products.

I claim:

1. A process for refining corn, the process comprising:
   (a) providing corn kernels having a moisture content of about 10 to 30 percent and comprising: (i) a pericarp comprising coarse fiber; (ii) an endosperm comprising soft starch, hard starch, protein, and fine fiber; and (iii) a germ;
   (b) steeping the corn kernels in recycled water from downstream processes, which water has a temperature of about 125 to 160° F., is essentially free of sulfurous acid and contains effective amounts of amylase enzymes, in a counter-current steeping reactor for about 10 to 20 hours to produce an aqueous slurry of steeped corn kernels having a moisture content of about 40 to 50 percent;
   (c) coarsely grinding the steeped corn kernels to produce a coarsely ground stream comprising coarse fiber, soft starch, hard starch-protein-fine fiber fragments, and germs;
   (d) heating the coarsely ground stream in the presence of effective amounts of amylase enzymes to gelatinize starch clinging to the coarse fiber and germs and to produce a partially gelatinized stream;
   (e) subjecting the partially gelatinized stream to sufficient shear and cavitation forces in the presence of effective amounts of amylase enzymes to gelatinize substantially all the starch and to produce a liquefied stream;
   (f) exposing the liquefied stream to effective amounts of amylase enzymes to produce a saccharified stream;
   (g) adding an effective amount of yeast to the saccharified stream and fermenting it to produce carbon dioxide and a fermented stream containing ethanol;
   (h) removing the carbon dioxide produced during fermentation and recycling some for gas lift agitation and blanketing; and
   (i) distilling the fermented stream to produce an ethanol stream and a bottoms stream.

2. The process of claim 1 wherein the liquefaction is conducted in a rotary homogenizer at a temperature of about 150 to 200° F. with a solids level of about 36 to 42 percent.

3. The process of claim 2 wherein effective amounts of protease enzymes are present in the steeping reactor and wherein the fermentation is conducted with essentially no addition of nitrogen compounds.

4. The process of claim 3 wherein effective amounts of cellulase enzymes are present in the steeping reactor and wherein the steeping is conducted with water having a temperature of about 140 to 155° F., a pH of about 3.8 to 6.5, and a solids level of about 9 to 14 percent.

5. The process of claim 4 wherein the soft starch is removed after coarse grinding and before partial gelatinization.

6. The process of claim 5 wherein the germs are removed after partial gelatinization and before liquefaction.

7. The process of claim 6 wherein the coarse fiber is removed after partial gelatinization and before liquefaction.

8. The process of claim 7 wherein the fine fiber and protein are removed after saccharification and before fermentation.

9. The process of claim 8 wherein the yeast is removed from the fermented stream and some is recycled.

10. The process of claim 9 wherein the corn kernels comprise whole corn kernels and grits, wherein the grits are removed from the whole corn kernels prior to steeping, and wherein the grits are added back to the partially gelatinized stream before liquefaction.

11. A process for refining corn, the process comprising:
   (a) providing corn kernels having a moisture content of about 10 to 30 percent and comprising: (i) a pericarp comprising coarse fiber; (ii) an endosperm comprising soft starch, hard starch, protein, and fine fiber; and (iii) a germ;
   (b) steeping the corn kernels in recycled water from downstream processes, which water has a temperature of about 140 to 155° F., is essentially free of sulfurous acid, and contains effective amounts of amylase, protease, and cellulase enzymes, in a counter-current steeping reactor for about 10 to 20 hours to produce an aqueous slurry of steeped corn kernels having a moisture content of about 40 to 50 percent;
   (c) coarsely grinding the steeped corn kernels to produce a coarsely ground stream comprising coarse fiber, soft starch, hard starch-protein-fine fiber fragments, and germs;
   (d) removing the soft starch from the coarsely ground stream;
   (e) heating the coarsely ground stream in the presence of effective amounts of amylase enzymes to gelatinize starch clinging to the coarse fiber and germs and to produce a partially gelatinized stream;
   (f) removing the germs from the partially gelatinized stream to produce a degermed stream;
   (g) removing the coarse fiber from the degermed stream to produce a hard starch-protein-fine fiber stream;
   (h) subjecting the hard starch-protein-fine fiber stream to sufficient shear and cavitation forces in the presence of effective amounts of amylase enzymes to gelatinize substantially all the starch and to produce a liquefied stream;
   (i) exposing the liquefied stream to effective amounts of amylase enzymes to produce a saccharified stream;
   (j) removing the fine fiber from the saccharified stream to produce a fiber-free saccharified stream;
   (k) removing the protein from the fiber-free saccharified stream to produce a fiber-and-protein-free saccharified stream;
   (l) adding an effective amount of yeast to the fiber-and-protein-free saccharified stream and fermenting it to produce carbon dioxide and a fermented stream containing ethanol;

(m) removing the carbon dioxide produced during fermentation and recycling some for gas lift agitation and blanketing;
(n) removing the yeast from the fermented stream to produce a yeast-free fermented stream; and
(o) distilling the yeast-free fermented stream to produce an ethanol stream and a bottoms stream.

12. The process of claim 11 wherein the fermentation is conducted with essentially no addition of nitrogen compounds.

13. The process of claim 12 wherein the liquefaction is conducted in a rotary homogenizer at a temperature of about 150 to 200° F. with a solids level of about 36 to 42 percent.

14. The process of claim 13 wherein the yeast is removed from the fermented stream and some is recycled.

15. The process of claim 14 wherein the steeping is conducted with water having a temperature of about 145 to 150° F., a pH of about 3.8 to 6.5, and a solids level of about 9 to 14 percent.

16. A process for refining grain, the process comprising:
(a) providing grain having a moisture content of about 10 to 30 percent and comprising a pericarp consisting essentially of coarse fiber; an endosperm consisting essentially of starch, protein, and fine fiber; and a germ;
(b) steeping the grain in recycled water from downstream processes, which water has a temperature of about 125 to 160° F., is free of sulfurous acid, and contains effective amounts of amylase, protease, and cellulase enzymes, in a counter-current steeping reactor for about 10 to 20 hours to produce an aqueous slurry of steeped grain having a moisture content of about 40 to 50 percent;
(c) coarsely grinding the steeped grain to produce a coarsely ground stream comprising coarse fiber fragments, endosperm fragments, and germs;
(d) heating the coarsely ground stream in the presence of effective amounts of amylase enzymes to gelatinize starch clinging to the coarse fiber fragments and germs and to produce a partially gelatinized stream;
(e) removing the germs from the partially gelatinized stream to produce a degermed stream;
(f) removing the coarse fiber from the degermed stream to produce a starch-protein-fine fiber stream;
(g) subjecting the starch-protein-fine fiber stream to sufficient shear and cavitation forces in a rotary homogenizer to gelatinize substantially all the starch and to produce a liquefied stream;
(h) exposing the liquefied stream to effective amounts of amylase enzymes to produce a saccharified stream;
(i) removing the fine fiber from the saccharified stream to produce a fiber-free saccharified stream;
(j) removing the protein from the fiber-free saccharified stream to produce a fiber-and-protein-free saccharified stream;
(k) adding an effective amount of yeast to the fiber-and-protein-free saccharified stream and fermenting it without the addition of nitrogen compounds to produce carbon dioxide and a fermented stream containing ethanol;
(l) removing the carbon dioxide produced during fermentation and recycling some for gas lift agitation and blanketing;
(m) removing the yeast from the fermented stream in a centrifugal separator to produce a yeast-free fermented stream; and
(n) distilling the yeast-free fermented stream to produce an ethanol stream and a bottoms stream.

17. The process of claim 16 wherein the fermentation is conducted with essentially no addition of nitrogen compounds.

18. The process of claim 17 wherein the liquefaction is conducted at a temperature of about 150 to 200° F. with a solids level of about 36 to 42 percent.

19. The process of claim 18 wherein the yeast is removed from the fermented stream and some is recycled.

20. The process of claim 19 wherein the steeping is conducted with water having a temperature of about 140 to 155° F., a pH of about 3.8 to 6.5, and a solids level of about 9 to 14 percent.

* * * * *